United States Patent
Guidera et al.

Patent Number: 5,733,291
Date of Patent: Mar. 31, 1998

[54] LONG BONE ALIGNMENT TOOL

[75] Inventors: Michael Guidera, Sacramento, Calif.;
Laurence Earl Dahners, Chapel Hill, N.C.

[73] Assignee: Hayes Medical, Incorporated, Sacramento, Calif.

[21] Appl. No.: 728,365

[22] Filed: Oct. 10, 1996

[51] Int. Cl.$^6$ .................................................. A61F 5/00
[52] U.S. Cl. .......................... 606/86; 606/105; 606/237
[58] Field of Search .......................... 606/237, 54, 55, 606/57, 59, 105, 97, 61, 86, 73; 602/39, 40

[56] References Cited

U.S. PATENT DOCUMENTS

| | | | |
|---|---|---|---|
| 1,759,514 | 5/1930 | Loose | 606/237 |
| 2,112,447 | 3/1938 | Peterson | 606/105 |
| 4,887,596 | 12/1989 | Sherman | 606/73 |
| 5,133,342 | 7/1992 | Seaton | 606/54 |
| 5,160,335 | 11/1992 | Wagenknecht | 606/57 |
| 5,207,676 | 5/1993 | Canadell et al. | 606/57 |
| 5,562,663 | 10/1996 | Wisnewski et al. | 606/73 |

*Primary Examiner*—Michael Buiz
*Assistant Examiner*—Julian W. Woo
*Attorney, Agent, or Firm*—Mark C. Jacobs

[57] ABSTRACT

A fracture reducing apparatus having a main rod comprising a handle section and a lever section and a pair of arms capable of riding on the lever section, each of which arms can be retained at a particular location in the lever section by the engagement of a thumb bolt disposed in the arm to frictionally engage the lever section. The apparatus is adapted to be autoclavable, and the use thereof reduces the incidence of radiation exposure from X-ray of the hands of the fracture reducing personnel. The device is used for the reduction of long bone fractures.

11 Claims, 3 Drawing Sheets

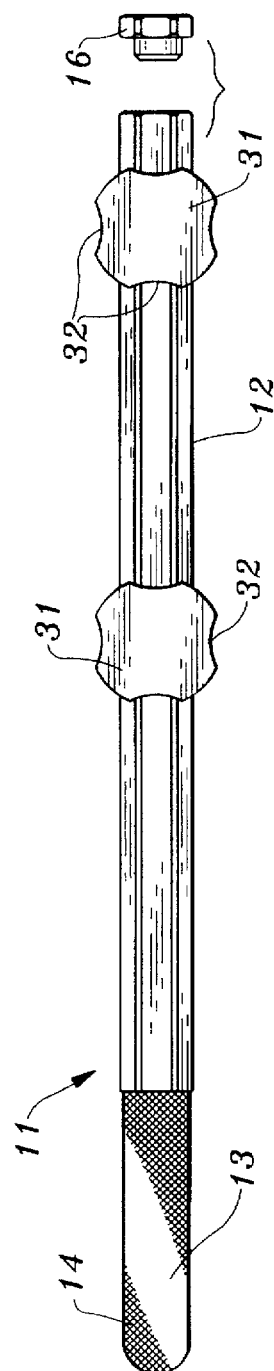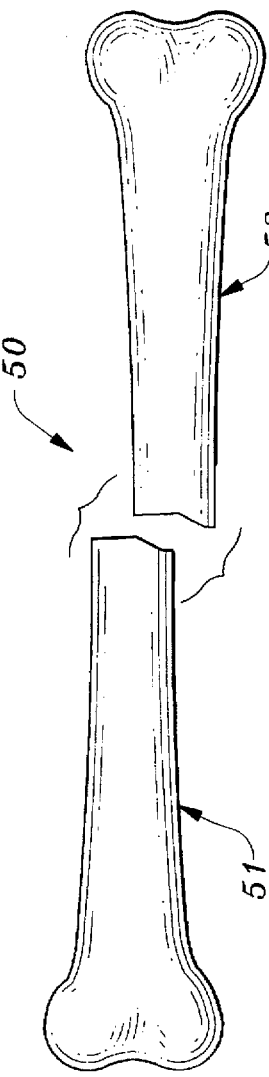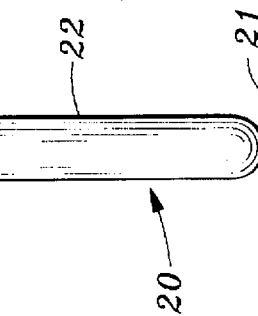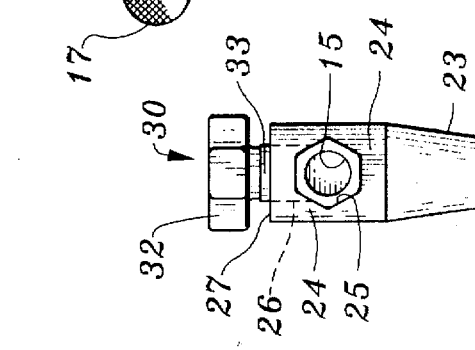

LONG BONE ALIGNMENT TOOL

FIELD OF THE INVENTION

This invention relates to the field of surgical tools and services and, more particularly, to an apparatus for the reduction of long bone fractures.

BACKGROUND OF THE INVENTION

It is well known in the medical community that the setting of fractures, technically known as fracture reduction, must be done under the guidance of X-ray using such techniques as bone fragment manipulation usually done by the hands of the surgeon or the technician. In view of the concern about excess radiation exposure due to repetitive efforts of such personnel on a multitude of patients, the medical industry has turned to the use of manipulator devices which will free the hands of emergency room or operating room personnel from radiation exposure by placing the hands out of the line of sight of the X-ray generator.

Among the prior art bone manipulators known to applicants are those found in the following U.S. Patents:

| 4,471,768 | Ciulo |
| 4,558,697 | Wu |
| 5,084,047 | Naraghi |

The Ciulo device is a pivoting V shape jaw member that is padded such as not to injure bone and muscle when force is applied to bring bone segments together.

Wu provides a retainer for one bone segment and a pair of oppositely directed cane-like members for pulling in opposite directions on adjacent bone sections to achieve alignment.

Naraghi uses a three pressure point fulcrum type device, which applies a top pressure at two spaced locations, with a bottom pressure being applied at a point between the two top points of pressure application. Pressure is applied by a trio of side arms.

It is an object therefore of this invention to provide a radiolucent leverage type fracture reducer.

It is another object to provide a low cost of manufacture and easy to use long bone fracture alignment apparatus.

It is yet another object to provide a fracture reducing apparatus that can be sized to the leg/arm of the patient.

It is still another object to provide a fracture reducer that is lightweight, portable, and which can be disassembled for easy storage if desired.

It is a further object of this invention to provide a fracture reducing apparatus which can be sterilized in an autoclave should such prove desirable or necessary.

Other objects of the invention will in part be obvious and will in part appear hereinafter.

The invention accordingly comprises the device possessing the features properties and the relation of components which are exemplified in the following detailed disclosure and the scope of the application of which will be indicated in the appended claims.

For a fuller understanding of the nature and objects of the invention reference should be made to the following detailed description, taken in conjunction with the accompanying drawings.

BRIEF DESCRIPTION OF THE FIGURES

FIG. 3 is an elevational end view of the bone aligning device of this invention.

FIG. 4 is a top plan view of the device of FIG. 1.

FIG. 5 is a schematic diagram of the condition of a typical broken bone, such as the femur prior to the use of this device.

FIG. 6 is a schematic diagram of the relationship of the two sections of the broken femur subsequent to use of this device.

SUMMARY OF THE INVENTION

A fracture reducing apparatus made of an autoclavable material, which reduces the fracture of long bones by bringing the two broken ends into alignment by the use of a levering action. The apparatus has two parallel arms each of which rides independently on a lever section of a main rod. The locus of placement on the lever section will regulate the pressure to be applied to that section of a broken bone to move it each into alignment with its counterpart section. Since the arms can be tightened on the main rod, such that the main rod's handle can be retained in a preset position by the user's hands out of the zone of x-ray, users will be more inclined to use this apparatus rather than other fracture reduction apparatuses for bone alignment.

DESCRIPTION OF THE PREFERRED EMBODIMENT

Figure 1:
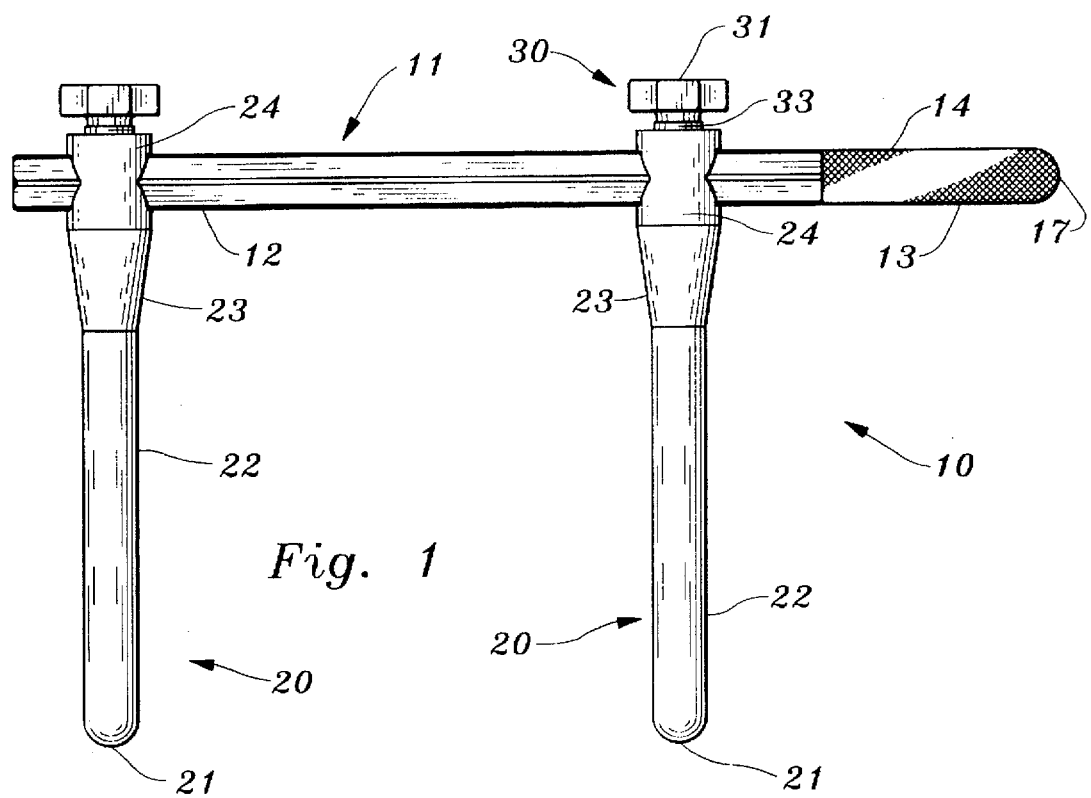
FIG. 1 is a left side elevational view of the device of this invention.

In FIG. 1 there is shown the fracture reduction apparatus of this invention. This apparatus 10, resembles a capital letter "F" in configuration, in that it has a main rod 11 and two normally disposed arms slidably mounted thereon, each of which is designated 20. Unlike the letter, the two arms are both moveable on the rod, and each arm is free to move independently of the other arm 20.

Figure 2:
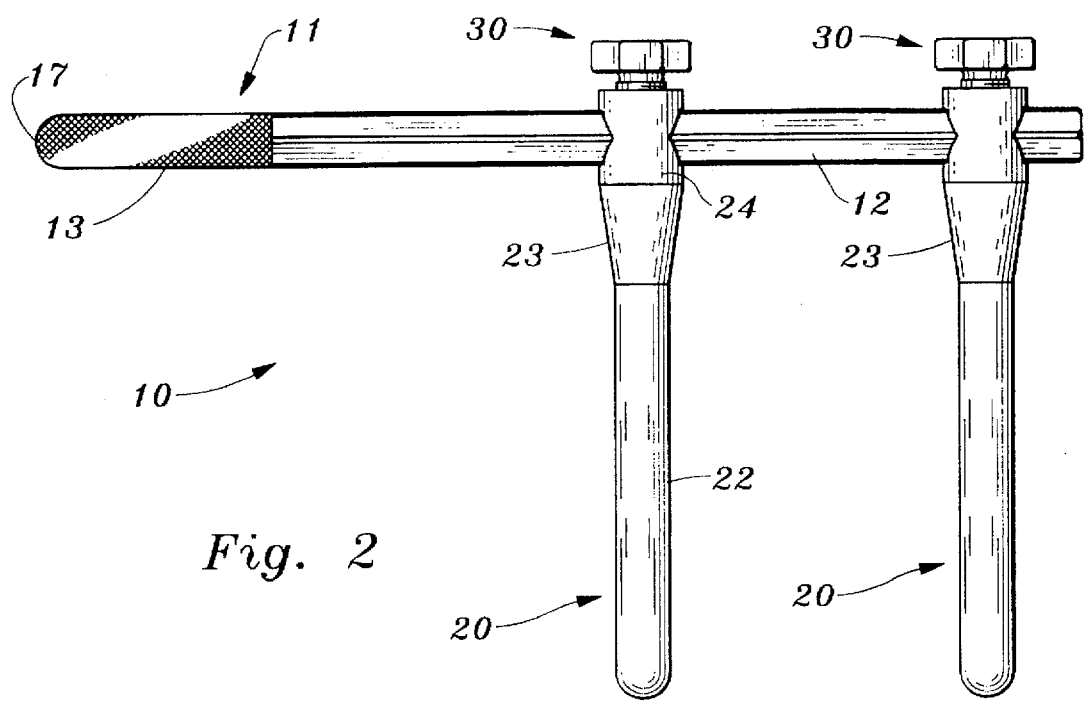
FIG. 2 is a right side elevational view thereof.

As is seen in FIGS. 1 and 2, the elevational views of the invention 10, the apparatus 10 comprises a main rod 11 which has a first lever section 12, and a second handle section 13 integrally aligned with said section 12. In order to present a face upon which a bolt can bind, lever section 12 should be of a cross section other than round. Here section 12 is seen to have a hexagonal cross section, but any shape from triangle to octagonal may be employed.

The handle cross section, however, is preferably round for ease of gripability. If desired, knurling may be applied to further enhance gripability of the surface 14.

Lever section 12 has an open end 15, but may be capped off by a plug 16 visible in other views.

Handle section 13 may have a domed end 17 for cosmetic purposes. The handle 13 may be formed integrally to the lever section or they may be threadedly attached to one another.

Each arm 20 is an elongated member adapted for receiving a tightening nut on one end and preferably domed at the other end to impede abrasion from an unintended impact. Preferably, each arm 20 has a proximal portion of a largest cross section designated the rider, 24. This rider portion 24 is preferably round on the periphery to avoid sharp edges. The rider portion includes a cross bore 25, which is sized slightly larger than and of the same configuration as the lever section 22 of the main rod 11. If the lever section 12 of the main rod 11 is hexagonal, then the cross bore is hexagonal to permit the rider portion 24 to ride freely along the length of the lever section. The rider 24 is given a larger cross section to provide adequate structural strength, due to the presence of the cross bore 25.

The rider portion 24 also has a linearly aligned threaded bore 26, on the end of the terminal end 27 of the rider portion, 24. This threaded bore 26 does communicate with the cross bore 25, and at a 90 degree angle. A thumb bolt 30 is disposed in threaded end bore 26. The thumb bolt 30 preferably has a handle 31 which fits easily into the hand of a user. To facilitate tightening, handle 31 has a plurality of recesses 33 therein, as for the thumb and third finger for example. The bolt 30 is of such a length that the threads 33 impact the lever section, such that when the bolt 30 is tightened, the rider 24 will be temporarily fixed at the locus on the lever section 12 of the main rod 11.

Figure 7:
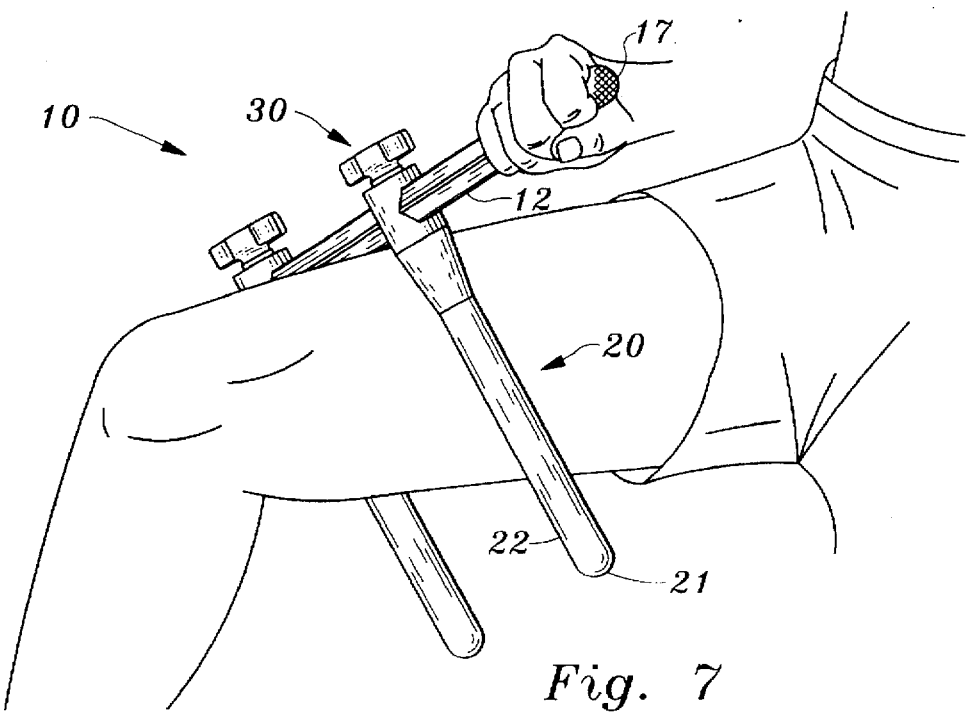
FIG. 7 is a right perspective view illustrating the use of the device of this invention.

Each arm 20's rider terminates in a narrowingly tapered intermediate portion 23 which leads to a linearly aligned elongated portion 22, this last mentioned portion being preferably of a preferably circular cross section. The provision of the tapered portion 13 also serves to prevent skin of a fleshy leg or arm from unintentionally being caught in the throughbore 25 if the lever 12 is placed close to the leg or arm as is seen in FIG. 7. The elongated portion 22 is preferably capped with a dome cap 21, again to guard against unintended injury. As is seen in the figures the two arms are preferably of the same length and are disposed in the same direction parallel to each other.

The pair of arms can be made as one size fits all, or in various sizes to fit, infants and young children, adolescents and adults as may be desired. If the later mode is chosen, then the length of the lever portion would be adjusted similarly to prevent the user from exerting excess pressure upon the bones of a young person.

The apparatus 10 which is intended for use in emergency medical facilities, operating rooms and other locations where open wounds are to be treated, must be made of a hygienic material. Thus Ultem™, a plastic, which is a polyimide made by General Electric is recommended if plastic is to be used. Apparatus 10 may also be made of thin wall aluminum, but not steel. While steel, such as stainless steel may be placed in an autoclave as is necessary to sterilize apparatus 10, steel is not roentgen ray transparent, and thus would show up on an x-ray diagram, thereby inhibiting viewing of the reduced fracture. A combination of plastic and metal can be used, if desired, as can composite materials, provided that the apparatus remains autoclavable and nonradiographic.

Figure 8:
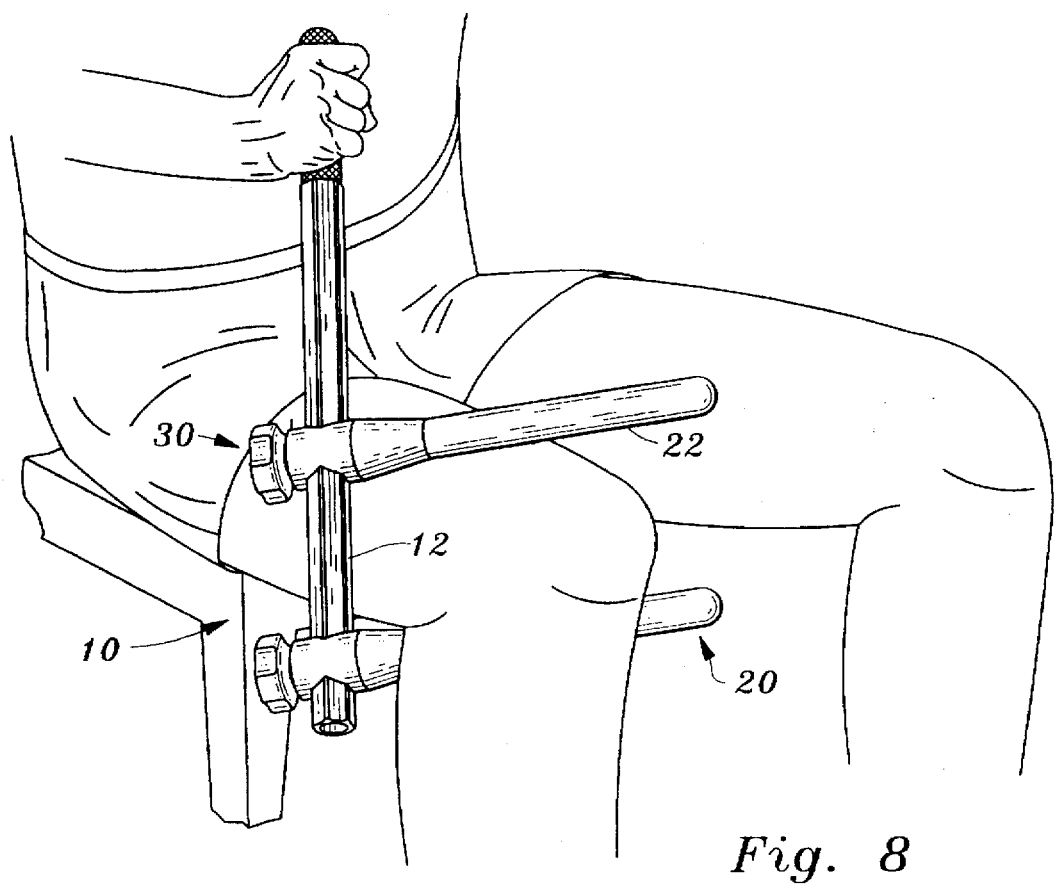
FIG. 8 is a left perspective view illustrating the use of this device to align the two sections of a broken femur.

The use of this apparatus is shown in FIGS. 7 and 8 on the thigh of an adult male. A first arm 20, is placed beneath the thigh and the second arm 20 above the thigh. This is accomplished by unloosening bolts 30, and adjusting the two rider portions such that one arm 20 is disposed on top of and one arm 20 is positioned just beneath the thigh. By rotating the apparatus either forward or backward as will be determined from a preexistent X-ray, on part of the broken bone 50, namely the upper part 51 can be moved downwardly or the lower part 52 can be moved upwardly as is deemed appropriate by the apparatus user. Ultimately it is desired that the two parts of the long bone 51, 52 be aligned as in FIG. 6.

The big advantage that this apparatus is believed to possess over the fracture reducing apparatus of Naraghi as disclosed and claimed in U.S. Pat. No. 5,084,047 is the fact that better control can be had by the user in that here each arm's location can be independently adjusted for placement to better control the application of reducing force, either upwardly or downwardly as may be needed.

In a typical model, intended for adult humans, the lever section may be made about 22 inches long, while each arm extends about 13 inches from end to end. A suitable configuration for the lever section 12 of the main rod 11 is hexagonal with each individual surface being about 1.75 inches in diameter. Good results have been obtained where the thumb bolt had a handle about 2 inches in diameter. Larger and smaller diameters for the thumb bolt are also acceptable.

The force can be applied preferably on the handle section or on the lever section of the main rod as may be desired. Yet the hands of the user, through proper placement of the arms of the apparatus, may be kept free from x-ray impact during the actual manipulation.

Thus, by using large handles on the thumb bolts it is easy to apply the frictional force to the lever section to prevent the movement of the rider on the lever section. And, the large handles on the thumb bolts also permit easy untightening and readjustment as may be needed.

The above recited description of this apparatus contains certain specific recitals which are intended solely to be illustrative of aspects of the invention and should not be deemed to be limiting of the scope of the invention. Thus while both arms are shown to be of the same length and cross section, they need not be so.

We claim:

1. A fracture reducing apparatus for reducing the fracture of long bones, which apparatus comprises:
   A) a main rod,
   B) a pair of parallel disposed arms which are adapted to ride on said main rod, said main rod having a handle section and a lever section, the handle section being of a first cross section and the lever section being of a different and solid cross section, said arms being disposed on said lever section and being similarly directed thereon, and wherein each of said arms includes means thereon to tighten the respective arm in a fixed position on said main rod's lever section.

2. The apparatus of claim 1 wherein the lever section is of a hexagonal configuration.

3. The apparatus of claim 1 wherein each of the parallel arms includes a proximal rider section, a narrowingly tapered second portion and an elongated third portion.

4. The apparatus of claim 3 wherein the elongated portion of each arm terminates in a domed cap.

5. The apparatus of claim 4 wherein each of the rider portions has a through cross bore for disposition of a lever section of the main rod, and said rider also has a linearly aligned end bore that communicates with the cross bore; and wherein a thumb bolt is disposed in said end bore, said thumb bolt being of a suitable length to frictionally engage said lever section when tightened.

6. An apparatus to reduce fractures of long bones, which apparatus comprises:
   (a) a main rod having a handle section and a lever section, where the handle section is of a first cross section and the lever section is of a different cross section,
   (b) a pair of independently moveable parallel arms adapted to ride on said lever section, both arms disposed in the same direction, on said lever section, wherein each arm comprises a proximal rider section having a cross through bore for receipt of said lever section, and a linearly aligned end bore that communicates with said cross through bore, each end bore carrying a thumb bolt for frictional engagement of said lever section.

7. The apparatus of claim 6 wherein the lever section of the main rod and the cross bore are each hexagonal.

8. The apparatus of claim 6 wherein the apparatus is autoclavable.

9. The apparatus of claim 4 wherein each domed elongated portion of each arm is of a circular cross section.

10. The apparatus of claim 6 wherein the two parallel arms are in the same plane relative to the main rod.

11. The apparatus of claim 6 wherein at least the arms thereof are of a roentgen ray transparent material.

* * * * *